United States Patent

Malekmehr et al.

[11] Patent Number: 5,616,126
[45] Date of Patent: Apr. 1, 1997

[54] LOW RESIDUAL BLADDER CATHETER

[76] Inventors: Farshad Malekmehr, 1321 Orleans St. #2001, Detroit, Mich. 48207; David A. Farah, 11105 McVine Ave., Sunland, Calif. 91040-2121

[21] Appl. No.: 397,975
[22] Filed: Mar. 3, 1995
[51] Int. Cl.$^6$ ................................................ A61M 29/00
[52] U.S. Cl. ................................................ 604/96; 604/54
[58] Field of Search ........................... 604/96, 264, 270, 604/280, 49, 54; 606/192, 194

[56] References Cited

U.S. PATENT DOCUMENTS

| | | | |
|---|---|---|---|
| 2,489,067 | 11/1949 | Wild | 604/270 |
| 4,043,346 | 8/1977 | Mobley et al. | |
| 4,217,903 | 8/1980 | Witherow | |
| 4,642,092 | 2/1987 | Moss | 604/43 |
| 4,684,369 | 8/1987 | Wildemeersch | |
| 4,863,424 | 9/1989 | Blake, III et al. | |
| 4,932,938 | 6/1990 | Goldberg et al. | 604/96 |
| 5,041,093 | 8/1991 | Chu | |
| 5,096,454 | 3/1992 | Samples | |
| 5,232,443 | 8/1993 | Leach | |
| 5,250,029 | 10/1993 | Lin et al. | |
| 5,300,022 | 4/1994 | Klapper et al. | |
| 5,306,226 | 4/1994 | Salama | 600/29 |
| 5,306,241 | 4/1994 | Samples | |

*Primary Examiner*—Corrine M. McDermott

[57] ABSTRACT

A bladder catheter comprising an elongate tubular body having a proximal portion with a proximal end, a distal portion, preferably between at least about 8 cm and 30 cm, with a distal end and a retaining portion with retaining mechanism disposed between the proximal portion and the distal portion. The tubular body of the bladder catheter further comprises a drainage lumen extending therethrough from a drainage port in the proximal end to at least one opening in the distal portion. The distal end of the catheter preferably comprises a weight. A method of continuously draining urine in a patient, comprising the steps of inserting a bladder catheter according to the present invention into the patient's urethra until the retaining mechanism and distal portion reside within the patient's bladder, actuating the retaining mechanism of the catheter, allowing the distal end of the catheter to fall into the dependent portion and, thereby, draining urine in the dependent portion of the bladder.

11 Claims, 2 Drawing Sheets

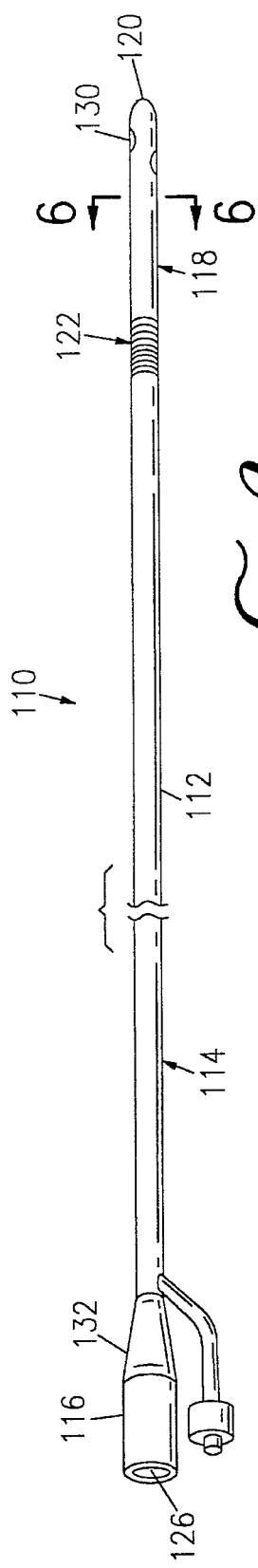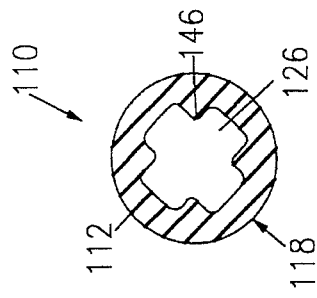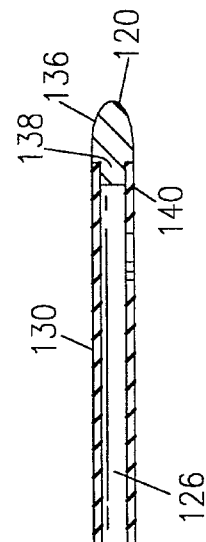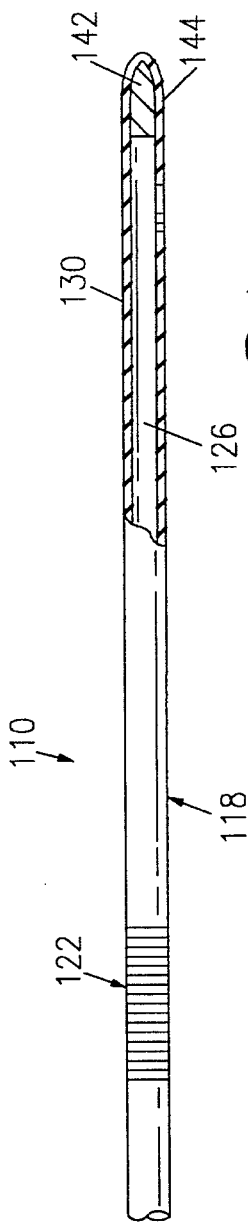

LOW RESIDUAL BLADDER CATHETER

BACKGROUND

Bladder catheters are routinely used for draining the urinary tract of patients who are unable to voluntarily urinate and in whom the accurate measurement of urine production is necessary. Commonly used bladder catheters have a number of problems associated with them. First, they do not completely drain the bladder because urine will collect in a dependent portion of the bladder, away from apertures in the distal catheter. This residual urine, in conjunction with the artificial passage created by the catheter, tends to produce urinary tract infections. These infections occur within hours to days after the initiation of continuous bladder drainage.

Further, measuring changes in urine output is critical to determining the cardiovascular and renal status of severely ill patients. Many of these patients are hospitalized in intensive care units and convalesce while supine. The supine position promotes collection of residual amount of urine in dependent portions of the bladder away from the opening of commonly used bladder catheters. In such patients, intermittent movement causes the residual amounts of urine to unpredictably contact the drainage opening of the catheter. This gives the impression that a large amount of urine was produced since the last measurement followed by substantially decreased production of urine as the urinary output flows again to the dependent portion of the bladder. Similarly, patients on rotating beds for the prevention and treatment of bed sores, such as with quadriplegics, will also appear to have irregular production of urine due to the unpredictable movement of significant amounts of urine to the catheter opening as the bed rotates. Thus, the accurate measurement of urine output is difficult with commonly used bladder catheters.

A number of bladder catheters have been developed that attempt to drain residual amounts of urine. Some of these have a drainage opening at the junction of the bladder and urethra. While some of these designs will drain urine when the junction is also the most dependent portion of the bladder, they do not drain residual urine from the dependent portions of the bladder away from the junction such as when the patient is horizontal. Thus, there remains a need for a bladder catheter that will continuously drain urine from the dependent portions of a bladder when the patient is supine.

SUMMARY

The present invention is directed to a bladder catheter that satisfies this need. The bladder catheter of the present invention comprises an elongate tubular body having a proximal portion with a proximal end, a distal portion with a distal end and a retaining portion with retaining mechanism. The retaining portion is disposed between the proximal portion and the distal portion. The catheter further comprises a drainage lumen through the tubular body extending from a proximal port in the proximal end to at least one opening in the distal portion. In one preferred embodiment, the catheter comprises a weight in the distal portion. In another preferred embodiment the distal portion of bladder catheter is between about 8 cm and about 30 cm. In still another preferred embodiment, the bladder catheter further comprises a support in the distal portion.

The present invention is also directed to a method of draining urine from a patient's bladder comprising the steps of inserting a bladder catheter according to the present invention into a patient's urethra until the retaining mechanism and distal portion reside within the patient's bladder, actuating the retaining mechanism of the catheter, and allowing the distal end of the catheter to enter urine in the dependent portion, thereby draining the urine from the patient. The method can further comprise the step of measuring the urine drained from the patient after the allowing step.

DRAWINGS

These and other features, aspects and advantages of the present invention will become better understood with regard to the following description, appended claims, and accompanying drawing where:

FIG. 3 is a fragmentary elevational view of the catheter shown in FIG. 2;

FIG. 4 is an elevational view of the retaining portion and distal portion according to one embodiment of the invention; and FIG. 5 is an elevational view of the retaining portion and distal portion according to another embodiment of the invention.

FIG. 6 is a cross-sectional view of the distal portion of the catheter shown in FIG. 3 taken along line 6—6.

DESCRIPTION

Figure 1:
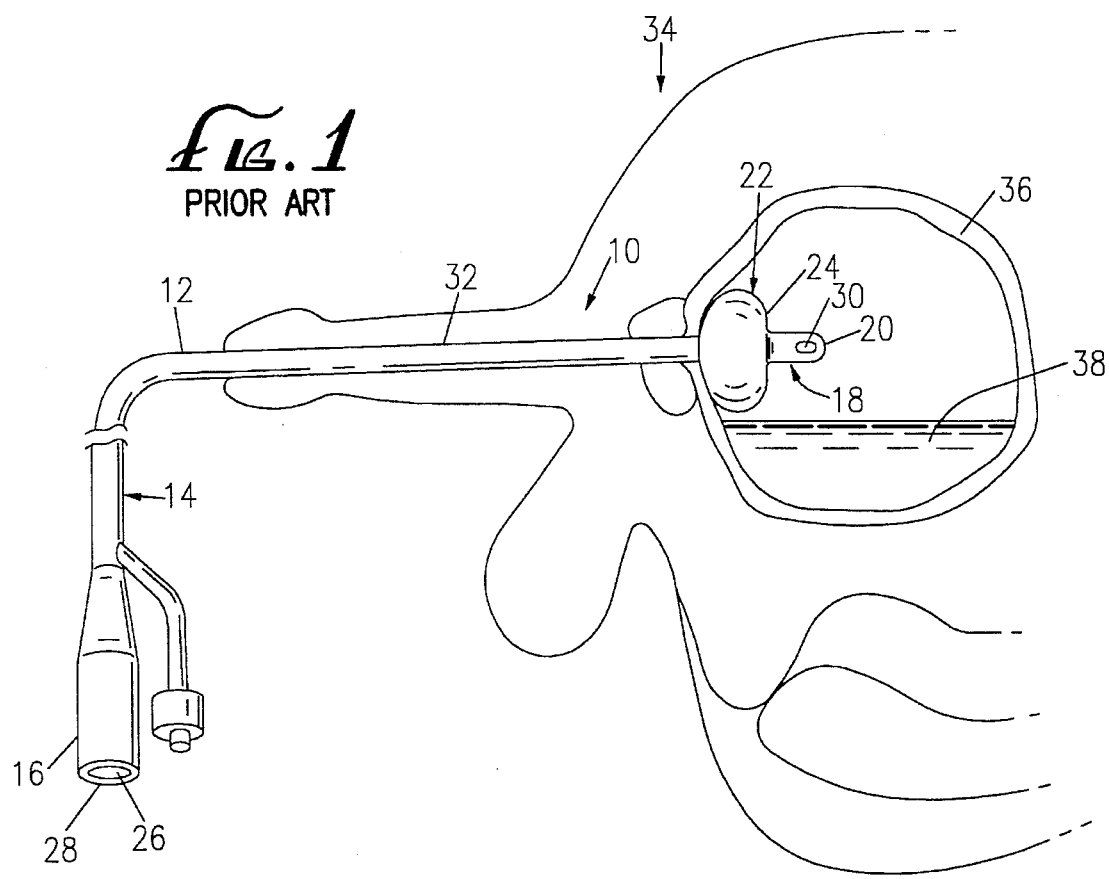
FIG. 1 is a perspective environmental view of a catheter as in known in the prior art.

Referring now to FIG. 1, there is illustrated a perspective environmental view of a bladder catheter 10 as is known in the prior art. The catheter comprises an elongate tubular body 12 having a proximal portion 14 with a proximal end 16, a distal portion 18 with a distal end 20 and a retaining portion 22 with retaining mechanism 24. The retaining portion 22 is disposed between the proximal portion 14 and the distal portion 18. The tubular body 12 of the bladder catheter 10 further comprises a drainage lumen 26 extending therethrough from a drainage port 28 in the proximal end 16 to at least one opening 30 in the distal portion 18.

In use, the distal end 20 of the bladder catheter 10 is inserted into the urethra 32 of a patient 34 and axially slid until the retaining portion 22 and the distal portion 18 reside within the bladder 36. Urine passing into the at least one opening 30 flows through the drainage lumen 26 and exits the drainage port 28 in the proximal end 16 of the catheter 10 for collection into a drainage bag, not shown. Urine in the dependent portion of the bladder 38, however, may not enter the at least one opening 30, especially if the patient 34 is supine.

Figure 2:
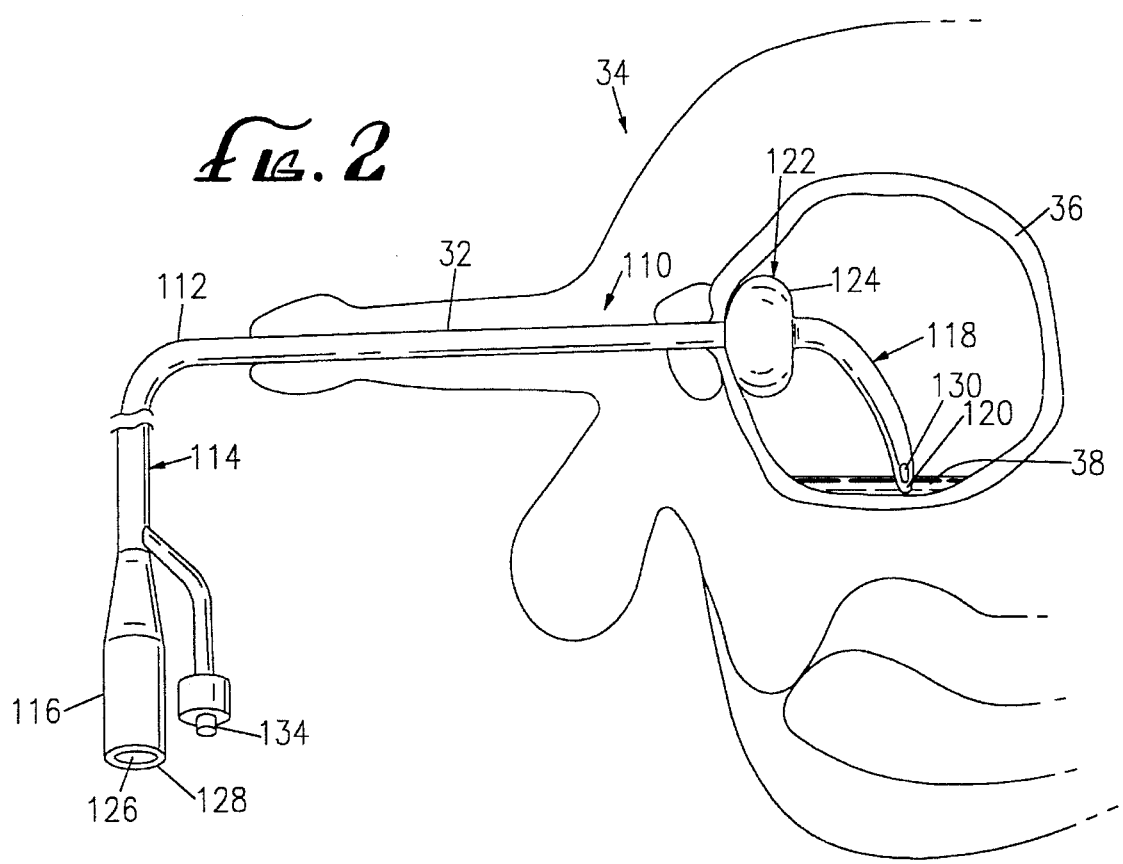
FIG. 2 is a perspective environmental view of a catheter embodying features of the invention.

Referring now to FIGS. 2 and 3, there is illustrated a perspective environmental and a fragmentary elevational view, respectively, of a catheter 110 embodying features of the invention. The catheter 110 comprises an elongate tubular body 112 having a proximal portion 114 with a proximal end 116, a distal portion 118 with a distal end 120 and a retaining portion 122 with retaining mechanism 124. The retaining portion 122 is disposed between the proximal portion 114 and the distal portion 118. The tubular body 112 of the bladder catheter 110 further comprises a drainage lumen 126 extending therethrough from a drainage port 128 in the proximal end 116 to at least one opening 130 in the distal portion 118.

The tubular body 112 can comprise any of a variety of biocompatible materials as are well known to those with skill in the art. The material is preferably flexible, but has enough stiffness for axial pushability during insertion. In one preferred embodiment the tubular body 112 comprises rubber.

The tubular body 112 can be any of a variety of cross-sectional areas and lengths such as are suitable for a variety of patients, ranging for newborn infants to large adults. In preferred embodiments, the cross-sectional area of the tubular body 112 ranges from about 5 Fr. to about 30 Fr. In a particularly preferred embodiment, the cross-sectional area ranges from about 12 Fr. to about 24 Fr.

The tubular body 112 can also be any of a variety of axial lengths such as are suitable for a variety of patients, ranging for newborn infants to large adults. In a preferred embodiment, the axial length of the tubular body 112 ranges from about 30 cm to about 75 cm.

The proximal end 116 of the bladder catheter 110 preferably comprises at least one adapter 132 for attaching to a drainage bag, not shown. Further, the proximal end 116 of the catheter 110 can comprise an actuator 134 for actuating the retaining mechanism 124. For example, when the retaining mechanism 124 is an inflation balloon, the actuator 134 comprises an adapter for an inflation syringe, not shown, or other inflation devices.

The length of the proximal portion 114 of the tubular body 112 can be any of a variety of lengths such as are suitable for a variety of patients. Preferably, the length of the proximal portion 114 is such that it comprises no more than approximately about 70% of the length of the tubular body 112. In a particularly preferred embodiment, the length of the proximal portion 114 comprises between about 60 and about 70% of the length of the tubular body 112.

The retaining portion 122 of the bladder catheter 110 is disposed between the proximal portion 114 and the distal portion 118 of the tubular body 112 and comprises a retaining mechanism 124. The retaining mechanism 124 can be any of a variety of devices known to those with skill in the art, such as reversible expanding prongs, mesh baskets or inflation balloons.

The length of the retaining portion 122 will depend on the retaining mechanism 124 utilized. In one preferred embodiment, the retaining mechanism 124 is an inflation balloon as shown in FIG. 2 and the length of the retaining portion 122 is about 2.5 cm in the uninflated state.

The length of the distal portion 118 of the tubular body 112 can be any of a variety of lengths such as are suitable for a variety of patients. Preferably, the length of the distal portion 118 is such that it comprises at least about 25% (twenty-five percent) of the length of the tubular body 112. In a particularly preferred embodiment, the length of the distal portion 118 comprises about 25% (twenty-five percent) of the length of the tubular body 112. Preferably the distal portion 118 is between about 8 cm and about 30 cm.

The distal portion 118 of the tubular body 112 comprises at least one opening 130 communicating with the drainage port 128 via the drainage lumen 126. The at least one opening 130 can be of any of a variety of shapes, but round or oval is preferred. The at least one opening 130 can be circumferentially reinforced to maintain patency. In one preferred embodiment, illustrated in FIG. 3, the at least one opening 130 is at least two openings. These at least two openings can be staggered axially, can be opposingly placed on the distal portion 118 or both. The distal end 120 of the catheter 110 is preferably tapered to facilitate catheterization.

Further, the distal portion 118 can comprise a weight. Preferably, the weight is incorporated into the distal end 120 of the distal portion 118 of the tubular body 112. The weight tends to cause the distal end 120 of the distal portion 118 of the tubular body 112 to submerge into urine 38 in the dependent portion of the bladder 36, thereby causing urine 38 to enter the at least one opening 130 in the distal portion 118.

The weight can comprise any of a variety of forms and materials. Preferably the form is such that it does not increase the cross-sectional area of the tubular body 112.

Referring now to FIG. 4 and 5, there are illustrated elevational views of two embodiments of the present invention showing examples of suitable configurations for weight, labeled 136 and 142 respectively. FIG. 4 shows a weight 136 forming the part of the distal end 120 of the catheter 110 and secured by a male proximal end 138 of the weight 136 fitting into a corresponding female segment 140 of the distal portion 118 of the catheter 110. FIG. 5 shows a similar arrangement but with the weight 142 covered by material 144 forming the distal end 120 of the tubular body 112. This later configuration is preferred because it lessens the chance of the weight 142 splitting from the catheter 110 body during use. Further, the weight can also comprise reinforcing structures, not shown, surrounding the at least one opening 130 in the distal portion 118 of the catheter.

Suitable material for the weight has a higher density than water. Preferably, the material is biocompatible and nonreactive to normal components of urine. Examples of suitable materials include lead, steel and titanium.

Depending on the length of the distal portion of the catheter 118 and the thickness and material of the tubular body 112, the catheter 110 may make a sharp bend at the junction of the retaining portion 122 and the distal portion 118, or along the distal portion 118. This sharp bend can close off the drainage lumen 126, thereby preventing urine flow. In order to obviate this problem, the catheter 110 can be provided with a support. Preferably, the support comprises a structure integrated into the internal wall of the drainage lumen 126 causing any bend in the distal portion 118 of the catheter 110 to form a gently sloping curve, thereby maintaining the patency of the drainage lumen 126. Suitable supports include an axially disposed internal rib or a circumferential spiral, extending in the tubular body from at least the retaining portion 122 to some or all of the distal portion 118. FIG. 6 is a cross-sectional view of the catheter 110 taken through line 6—6 in FIG. 3 showing a support comprising four circumferentially-spaced, axially-oriented internal ribs 146 integrated into the tubular body 112. Alternately, one or more axially-spaced, circumferential-oriented ribs, not shown, can be incorporated as suitable supports. Further, gradually varying wall thickness can be provided for the support, also not shown, where the wall is thicker proximal from the junction of the retaining mechanism and distal portion, and gradually gets thinner distally. Other supports will be equally appreciated by those with skill in the art, with reference to the disclosure herein.

The bladder catheter 110 according to the present invention is used as follows. The distal end 120 of the bladder catheter 110 is inserted into the urethra 32 of a patient 34 and axially slid until the retaining portion 122 and the distal portion 118 reside within the bladder 36. The retaining mechanism 124 is then actuated, thereby causing retention of the distal portion 118 of the catheter 110 within the bladder 36.

The relatively long length of the distal portion 118 of the catheter 110 allows the at least one opening 130 to fall by gravity into the dependent portion of the bladder. This allows urine 38 in the dependent portion of the bladder 36 to enter the at least one opening 130 and pass into the drainage lumen 126 to empty out of the catheter 110 via the proximal port 128. Drainage occurs through a combination of gravity and siphoning, though suctioning can be used as is known by those with skill in the art. Urine output is then intermittently measured, such as by collection in a drainage bag, not shown. Accurate measurement of urine output is thereby accomplished. According to another embodiment of the present invention, weight in the distal portion 118 of the catheter 110 assists the distal portion 118 to drop into the dependent portion of the bladder increasing the accuracy of urine output measurement. When no longer needed, the retaining mechanism 124 is unactuated and the catheter 110 slid axially outwards.

Although the present invention has been described in considerable detail with reference to certain preferred versions thereof, other versions are possible. For example, the catheter 110 can include an anti-bacterial coating to inhibit the introduction of infectious organisms into the bladder. Therefore, the spirit and scope of the appended claims should not be limited to the description of the preferred embodiments contained herein.

We claim:

1. A bladder catheter, comprising:

an elongate tubular body having a proximal portion with a proximal end, a distal portion with a distal end, a retaining portion disposed between the proximal portion and the distal portion, a drainage lumen therethrough, and a support within the tubular body;

wherein the retaining portion has a retaining mechanism affixed to the tubular body;

wherein the proximal portion has a proximal port;

wherein the distal portion has an axial length;

wherein the distal portion has at least one opening therein;

wherein the drainage lumen extends from the proximal port in the proximal end to the at least one opening in the distal portion; and wherein the support substantially prevents closure of the drainage lumen from axial bending of the distal portion.

2. The bladder catheter of claim 1, wherein the distal end includes a weight.

3. The bladder catheter of claim 2, wherein the weight comprises material selected from the group consisting of lead, steel and titanium.

4. The bladder catheter of claim 2, wherein the weight has a density higher than water.

5. The bladder catheter of claim 1, wherein the axial length of the distal portion is at least about 8 cm.

6. The bladder catheter of claim 1, wherein the support comprises at least two circumferentially-spaced, axially-oriented ribs in the tubular body.

7. The bladder catheter of claim 1, wherein the axial length of the distal portion is at least about 20 cm.

8. The bladder catheter of claim 1, wherein the retaining mechanism is an inflation balloon and the elongate tubular body further comprises an inflation lumen therein extending from the proximal portion to the inflation balloon.

9. The bladder catheter of claim 1, wherein the at least one opening in the distal portion is two openings, each opening communicating with the drainage lumen.

10. A method of draining urine from a patient's bladder, comprising the steps of:

(a) inserting a bladder catheter according to claim 1 into a patient's urethra until the retaining mechanism and distal portion reside within the patient's bladder, wherein the bladder comprising a dependent portion;

(b) actuating the retaining mechanism of the catheter; and (c) allowing the distal end of the catheter to enter urine in the dependent portion, thereby draining the urine from the patient.

11. The method of claim 10 further comprising the step of measuring the urine drained from the patient after the allowing step.

* * * * *